United States Patent
Yamada et al.

(10) Patent No.: US 6,486,353 B2
(45) Date of Patent: Nov. 26, 2002

(54) PROCESS FOR PRODUCING OPTICALLY ACTIVE 3,7-DIMETHYL-6-OCTENOL AND PROCESS FOR PRODUCING INTERMEDIATE THEREFOR

(75) Inventors: Shinya Yamada, Kanagawa (JP); Yoshiki Okeda, Kanagawa (JP); Yoji Hori, Kanagawa (JP); Toshimitsu Hagiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 10/098,358

(22) Filed: Mar. 18, 2002

(65) Prior Publication Data

US 2002/0128525 A1 Sep. 12, 2002

Related U.S. Application Data

(62) Division of application No. 09/827,334, filed on Apr. 6, 2001.

(30) Foreign Application Priority Data

Apr. 7, 2000 (JP) ........................................ 2000-106649

(51) Int. Cl.⁷ ......................... C07C 209/60; C07C 35/00
(52) U.S. Cl. .................... 564/485; 568/875; 568/909.5
(58) Field of Search ............................... 564/408, 485; 568/875, 909.5

(56) References Cited

U.S. PATENT DOCUMENTS

| 4,186,148 A | 1/1980 | Murata et al. |
| 4,604,474 A | 8/1986 | Kumobayasi et al. |

FOREIGN PATENT DOCUMENTS

| JP | 49-48610 | 5/1974 |
| JP | 51-4109 | 1/1976 |
| JP | 53-135912 | 11/1978 |
| JP | 53-141205 | 12/1978 |
| JP | 1-42959 | 9/1989 |

OTHER PUBLICATIONS

English Abstract JP 49–48610, May 11, 1974.
English Abstract JP 51–4109, Jan. 14, 1976.
English Abstract JP 53–135912, Nov. 28, 1978.
English Abstract JP 53–141205, Dec. 8, 1978.
English Abstract JP 1–42959, Sep. 18, 1989.

*Primary Examiner*—Sreeni Padmanabhan
(74) *Attorney, Agent, or Firm*—Sughrue Mion, PLLC

(57) ABSTRACT

Cis-3,7-dimethyl-2,7-octadienylamine containing from 2 to 10% by weight cis-3,7-dimethyl-2,7-octadienylamine is prepared by subjecting a mixture of an alkylamine and isoprene in a molar ratio of 1:4 to 1:4.5 to telomerization at 80 to 100° C. for from 2.5 to 3.5 hours in the presence of an alkyllithium catalyst and/or phenyllithium catalyst.

5 Claims, No Drawings

PROCESS FOR PRODUCING OPTICALLY ACTIVE 3,7-DIMETHYL-6-OCTENOL AND PROCESS FOR PRODUCING INTERMEDIATE THEREFOR

This is a divisional of application Ser. No. 09/827,334 filed Apr. 6, 2001; the disclosure of which is incorporated herein by reference.

FIELD OF THE INVENTION

The present invention relates to a process for producing optically active 3,7-dimethyl-6-octenol which contains from 2 to 10% by weight optically active 3,7-dimethyl-7-octenol and is useful as a material for perfumes, etc. The invention further relates to a process for producing a cis-3,7-dimethyl-2,6-octadienylamine compound (hereinafter referred to simply as "nerylamine compound") containing from 2 to 10% by weight cis-3,7-dimethyl-2,7-octadienylamine compound (hereinafter referred to simply as "α-nerylamine compound"), these amine compounds being intermediates for those optically active compounds.

The optically active 3,7-dimethyl-6-octenol provided by the invention, which contains from 2 to 10% by weight optically active 3,7-dimethyl-7-octenol, has an elegant rosy fragrance and is extremely useful for fragrance impartation to aromatic articles.

BACKGROUND OF THE INVENTION 3,7-Dimethyl-6-octenol (hereinafter referred to also as "citronellol") has conventionally been known as a material for rosy perfumes, and the d-, l-, and dl-isomers have already come to be produced and practically used [Motoichi Indo, Gôsei Kôryô(Kagaku To Shôhin Chishiki), Kagaku Kogyo Nippo Sha, 1996]. Such perfume substances are not limited to alcohols These compounds, even when slightly different in structure, can generally have utterly different fragrances and differ also in properties, e.g., the ability to be retained and volatility. Consequently, for obtaining a new perfume, it is highly important to synthesize many compounds and investigate their fragrances.

Disclosed as processes for producing a nerylamine compound through the telomerization of isoprene with an amine compound are a method in which an n-butyllithium catalyst is used (JP-A-49-48610 (the term "JP-A" as used herein means an "unexamined published Japanese patent application")), a method in which a catalyst prepared from a secondary amine, a conjugated olefin, and lithium metal is used (JP-A-51-4109), a method in which a catalyst prepared from a secondary amine, a polynuclear aromatic compound and/or a polyphenyl compound, and lithium metal is used (JP-A-53-135912), and a method in which a catalyst prepared from a secondary amine, a conjugated diene compound and/or polycyclic aromatic compound as an unsaturated hydrocarbon, a lithium salt, and sodium metal and/or potassium metal is used (U.S. Pat. No. 4,186,148).

However, the method disclosed in JP-A-49-48610 has the following drawbacks. The method necessitates a reaction time as long as from 5.5 to 24 hours despite the use of an n-butyllithium catalyst and has low selectivity to nerylamine. Consequently, it is difficult to apply the method to an industrial process for continuously conducting the reaction and this application is costly.

The method disclosed in JP-A-51-4109 has attained a yield as high as about 85% using a different lithium catalyst. However, a reaction time of 18 hours is necessary for attaining the yield. This method also is difficult to practice industrially.

The method disclosed in JP-A-53-135912 has succeeded in obtaining nerylamine in a yield of 86.4% by using a different lithium catalyst to react an amine with isoprene in a proportion of 1:5 at 80° C. for 3 hours. However, since the isoprene amount is excessively large as compared with the amine amount, there have been problems concerning the recovery of isoprene and the yield of nerylamine.

The method disclosed in U.S. Pat. No. 4,186,148 has succeeded in obtaining nerylamine in a yield of 85% by reacting an amine with isoprene in a proportion of 1:5 first at 65° C. for 1 hour and then at 80° C. for 4 hours. However, since the isoprene amount is excessively large as compared with the amine amount, there have been problems concerning the recovery of isoprene and the yield of nerylamine. In addition, this method is unsuitable for continuous reaction because preparation of the lithium catalyst necessitates use of a dangerous metal such as sodium or potassium Furthermore, although JP-A-49-48610 discloses an N,N-dialkyl(3-methyl-2-butenyl)amine (formula 5), an N,N-dialkyl(2-methyl-2-butenyl)amine (formula 6), and an N,N-dialkyl(2-isopropenyl-5-methyl-4-hexenyl)amine (formula 7), which are yielded as by-products by the method disclosed therein there are no descriptions therein concerning the α-nerylamine represented by formula 4 in the invention. No descriptions concerning by-products are given in the specification of the other references cited above.

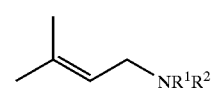

(5)

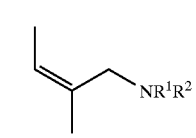

(6)

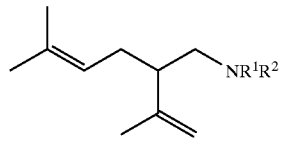

(7)

In a conventional method for asymmetrically isomerizing a cis-dialkyloctadienylamine obtained, the amine is isomerized in tetrahydrofuran using a rhodium-BINAP catalyst and then hydrolyzed with sulfuric acid to obtain an aldehyde (see U.S. Pat. No. 4,604,474)

The present inventors made intensive investigations on methods for synthesizing optically active 3,7-dimethyl-6-octenol (citronellol), which is useful as a material for rosy perfumes. During these investigations, they have found that when the telomerization of an alkylamine with isoprene, which is known as a process for producing cis-3,7-dimethyl-2,6-octadienylamine (a nerylamine compound) serving as an intermediate for citronellol, is conducted under strictly selected reaction conditions, then cis-3,7-dimethyl-2,7-octadienylamine (an α-nerylamine compound) serving as an intermediate for optically active 3,7-dimethyl-7-octenol, which also is useful as a material for rosy perfumes, is yielded in a large amount.

The inventors have further found that asymmetrically isomerizing the mixture of nerylamine and α-nerylamine in the same manner as in the reaction step of synthesis of citronellol from nerylamine, subsequently hydrolyzing the mixture, and reducing the resultant citronellal mixture gives a mixture comprising optically active 3,7-dimethyl-7-octenol and optically active 3,7-dimethyl-6-octenol (citronellol) and this mixture is more useful as a material for rosy perfumes than conventional ones. The invention has been completed based on this finding.

SUMMARY OF THE INVENTION

An object of the invention is to provide a process for stably producing optically active 3,7-dimethyl-6-octenol which contains from 2 to 10% by weight optically active 3,7-dimethyl-7-octenol and is extremely useful as a material for rosy perfumes. Another object of the invention is to provide a process for efficiently producing a cis-3,7-dimethyl-2,6-octadienylamine compound (nerylamine compound) containing from 2 to 10% by weight cis-3,7-dimethyl-2,7-octadienylamine compound (α-nerylamine compound), these amine compounds being useful as materials for those optically active compounds.

The invention, which makes it possible to stably produce the above-described optically active 3,7-dimethyl-6-octenol (citronellol) containing from 2 to 10% by weight optically active 3,7-dimethyl-7-octenol, includes the following.

(1) A process for producing optically active 3,7-dimethyl-6-octenol, a compound having an excellent fragrance represented by formula (1),

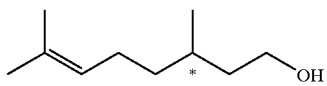

(1)

containing from 2 to 10% by weight optically active 3,7-dimethyl-7-octenol represented by formula (2):

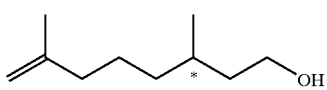

(2)

which comprises subjecting a mixture of an alkylamine and isoprene in a molar ratio in the range of from 1:4 to 1:4.5 to telomerization at a reaction temperature of from 80 to 100° C. for from 2.5 to 3.5 hours in the presence of an alkyllithium catalyst and/or phenyllithium catalyst to thereby prepare a nerylamine compound represented by general formula (3):

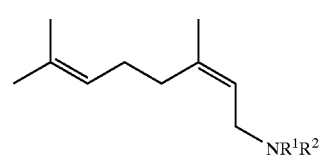

(3)

wherein $R^1$ and $R^2$ each represents a hydrogen atom or an alkyl, aralkyl, or aryl group having 1 to 10 carbon atoms, containing from 2 to 10% by weight α-nerylamine compound represented by general formula (4):

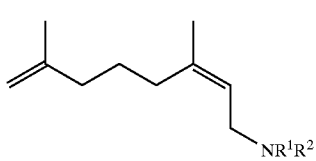

(4)

wherein $R^1$ and $R^2$ each represents a hydrogen atom or an alkyl, aralkyl, or aryl group having 1 to 10 carbon atoms, asymmetrically isomerizing the resultant reaction product mixture, subsequently hydrolyzing the mixture to obtain a citronellal mixture, and then reducing the citronellal mixture.

(2) A process for producing a nerylamine compound represented by general formula (3):

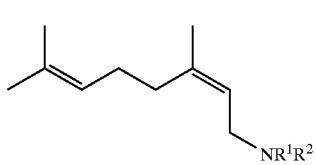

(3)

wherein $R^1$ and $R^2$ each represents a hydrogen atom or an alkyl, aralkyl, or aryl group having 1 to 10 carbon atoms, useful as an intermediate for 3,7-dimethyl-6-octenol, which contains from 2 to 10% by weight α-nerylamine compound represented by general formula (4):

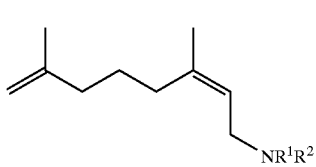

(4)

wherein $R^1$ and $R^2$ each represents a hydrogen atom or an alkyl, aralkyl, or aryl group having 1 to 10 carbon atoms, which comprises subjecting a mixture of an alkylamine and isoprene in a molar ratio of from 1:4 to 1:4.5 to telomerization at a reaction temperature of from 80 to 100° C. for from 2.5 to 3.5 hours in the presence of an alkyllithium catalyst and/or phenyllithium catalyst.

DETAILED DESCRIPTION OF THE INVENTION

The invention will be explained below in detail.

Examples of the amine compound to be used in the invention include dimethylamine, diethylamine, di-n-propylamine, diisopropylamine, di-n-butylamine, cyclohexylamine, piperidine, pyrrolidine, and morpholine. Of these, dimethylamine, diethylamine, di-n-propylamine, and diisopropylamine are preferred.

The amount of the isoprene to be added is preferably from 3 to 5 times by mole, more preferably from 4 to 4.5 times by mole, the amount of the amine compound.

Examples of the lithium catalyst include methyllithium, n-butyllithium, sec-butyllithium, tert-butyllithium, and phenyllithium. Of these, n-butyllithium is preferred. The amount of the lithium catalyst to be used in the telomerization may be from 0.5 to 5 mol % based on the amine compound to be subjected to the reaction.

The telomerization reaction of the starting amine compound with isoprene for producing a nerylamine compound containing from 2 to 10%, preferably from 3 to 6% α-nerylamine compound can be accomplished by introducing the lithium catalyst and the amine compound and isoprene as starting materials into the same reactor simultaneously or successively.

The reaction is conducted in an inert atmosphere with or without a solvent. In the case of using a solvent, the solvent is one in which the lithium compound used as a catalyst can dissolve. Examples of solvents which can be used include hydrocarbon solvents such as benzene and toluene and ether solvents such as tetrahydrofuran.

The temperature for the reaction is generally from 50 to 120° C., preferably from 80 to 100° C. The reaction is conducted for generally from 2 to 6 hours, preferably from 2.5 to 3.5 hours.

Subsequently, water, ethanol, $CO_2$, or the like is added to the reaction mixture resulting from the telomerization of the starting isoprene with the starting amine compound conducted under the reaction conditions described above, whereby the lithium compound used as a catalyst is deactivated. Thereafter, the oil layer is distilled to thereby recover a nerylamine fraction containing from 2 to 10% α-nerylamine compound.

The thus-obtained nerylamine fraction containing from 2 to 10% α-nerylamine compound is subjected to an asymmetric isomerization reaction.

The asymmetric isomerization reaction is conducted in a solvent in an inert atmosphere such as, e.g., nitrogen using a known catalyst for asymmetric isomerization.

As the solvent may be used an ether such as tetrahydrofuran, a ketone such as acetone, or the like- As the catalyst can be used a rhodium-phosphine complex catalyst (see JP-B-1-42959) or a catalyst such as [Rh (COD) (BINAP) ]$ClO_4$, [Rh (BINAP) $_2$]$ClO_4$, [Rh (BINAP) $_2$]OTf, [Rh (COD) (t-BINAP) ]$ClO_4$, [Rh(t-BINAP) $_2$]$ClO_4$, or [Rh(t-BINAP)$_2$]OTf, wherein "BINAP" means a 2,2'-bis (diphenylphosphino)-1,1'-binaphthyl group, "t-BINAP" means a 2,2'-bis (di-p-tolylphosphino) -1,1 '-binaphthyl group, and "OTf" means a triflate group.

The reaction temperature is generally from 50 to 130° C., preferably from 100 to 110° C. After completion of the reaction, the reaction mixture is transferred to a distiller, where the solvent is removed by vacuum distillation to obtain a geranyl enamine compound (citronellal enamine compound) as an isomerization reaction product.

The geranyl enamine compound obtained by the asymmetric isomerization reaction is subjected to a hydrolysis reaction and thereby converted to a citronellal compound.

The hydrolysis reaction is an acid hydrolysis reaction. Although either an organic acid or an inorganic acid can be used as the acid, it is preferred to use an inorganic acid such as sulfuric acid or hydrochloric acid.

The hydrolysis reaction is conducted by dissolving the geranyl enamine compound in an inert solvent, e.g., toluene, and then adding an acid, e.g , sulfuric acid, to the solution to treat the enamine compound at a temperature of about from 0 to 10° C. in an ordinary manner The citronellal compound obtained by the hydrolysis reaction is subjected to a catalytic hydrogenation reaction in an ordinary manner. Thus, the citronellal compound, which is an aldehyde compound, is converted to an optically active citronellol compound which is an alcohol compound.

This reaction is conducted with stirring using a catalyst ordinarily used for reactions for hydrogenating aldehyde compounds into alcohol compounds, such as, e.g., a copper-chromium catalyst, palladium catalyst, or Raney nickel catalyst.

Finally, the catalyst is removed from the hydrogenation reaction mixture, which is then subjected to vacuum distillation. Thus, the target citronellol compound is obtained.

EXAMPLES

The invention will be explained below in detail by reference to Examples and Comparative Examples. However, the invention should not be construed as being limited by these Examples in any way- Various modifications can be made unless they depart from the scope of the invention.

1) Reaction Products were Examined by Gas Chromatography (GLC) Under the Following Conditions Analytical instrument used: gas chromatograph G5000, manufactured by Hitachi Ltd.

Column: TC-1 (0.25 mm×30 m), manufactured by GL Sciences

Detector: FID (Flame Ionization Detector)

2) Reaction Products were Identified by $^1$H-NMR Spectroscopy Based on a Comparison with Data Given in the Literature $^1$H-NMR: DRX-500 ($^1$H, 500 MHz), manufactured by Bruker Instruments Inc.

Example 1

Synthesis of Cis-3,7-dimethyl-2,6-octadienyl-diethylamine (Neryldiethylamine) Containing 6 wt % Cis-3,7-dimethyl-2,7-octadienyldiethylamine (α-Neryldiethylamine)

A solution prepared by mixing 2.93 g (40.0 mmol) of diethylamine with 18.0 ml (180 mmol) of isoprene was introduced into a 100-ml pressure tube in a nitrogen atmosphere- Thereto was gradually added dropwise at 0° C. a solution (1.6 M solution) prepared by dissolving 0.064 g of n-butyllithium (1.0 mmol) in 0.63 ml of hexane. This mixture was stirred first at room temperature for 15 minutes and then at 90° C. for 2.5 hours. To the resultant reaction mixture was added 0.3 ml of water to deactivate the catalyst. After liquid separation, the organic layer was separated and distilled to recover the unreacted isoprene. Subsequently, the concentrate remaining after the isoprene recovery was distilled under reduced pressure to obtain 7.29 g (34.8 mmol; GC yield, 87.0%) of the target mixture comprising α-neryldiethylamine and neryldiethylamine.

Boiling point, 83–85° C./400 Pa. Neryldiethylamine $^1$H-NMR(CDCl$_3$) δ1.03 (6H, T, J=7.1 Hz), 1.61 (3H, s), 1.68 (3H, s), 1.72 (3H, m), 2.07 (4H, m), 2.50 (4H, t, J=7.1 Hz), 3.04 (2H, d, J=6.8 Hz), 5.11 (1H, m), 5.26 (1H, m). α-Neryldiethylamine $^1$H-NMR(CDCl$_3$) δ1.03 (6H, T, J=7.1 Hz), 1.61 (3H, s) 1.68 (3H, s), 1.72 (3H, m), 2.07 (4H, m), 2.50 (4H, t, J=7.1 Hz), 3.04 (2H, d, J=6.8 Hz), 4.68 (1H, m), 4.71 (1H, m), 5.26 (1H, m)

Example 2

Synthesis of Neryldiethylamine Containing 6 wt % α-Neryldiethylamine

The same procedure as in Example 1 was conducted, except that the high-temperature stirring was conducted at 90° C. for 3 hours. Thus, the target compound was obtained in an amount of 7.16 g (34.2 mmol; GC yield, 85.5%).

Example 3

Synthesis of Neryldiethylamine Containing 5 wt % α-Neryldiethylamine

The same procedure as in Example 1 was conducted, except that the high-temperature stirring was conducted at 80° C. for 3 hours. Thus, the target compound was obtained in an amount of 6.85 g (32.7 mmol; GC yield, 81.8%).

Example 4

Synthesis of Neryldiethylamine Containing 5 wt % α-Neryldiethylamine

The same procedure as in Example 1 was conducted, except that the high-temperature stirring was conducted at 80° C. for 3.5 hours. Thus, the target compound was obtained in an amount of 7.19 g (34.3 mmol; GC yield, 85.8%).

Example 5

Synthesis of Neryldiethylamine Containing 6 wt % α-Neryldiethylamine

The same procedure as in Example 1 was conducted, except that 16.0 ml (160 mmol) of isoprene was used in place of 18.0 ml (180 mmol) of isoprene and that the high-temperature stirring was conducted at 90° C. for 3 hours. Thus, the target compound was obtained in an amount of 6.49 g (31.0 mmol; GC yield, 77.4%).

Example 6

Synthesis of Neryldiethylamine Containing 6 wt % α-Neryldiethylamine

Into a 5-L autoclave were introduced 365.6 g (5.0 mol) of diethylamine and 1,532 g (22.5 mol) of isoprene in a nitrogen atmosphere. Thereto was added 78.1 ml of a hexane solution (1.6 M solution) of n-butyllithium (125 mmol) with a syringe at 11° C. The resultant mixture was heated to 90° C. over 35 minutes. This reaction mixture was stirred at 90° C. for 2.5 hours and then rapidly cooled to 15° C. Thereto was added 40 ml of water This mixture was stirred at around 10° C. for 1.5 hours. After liquid separation, the organic layer was distilled to obtain 843.4 g (4.03 mol; isolation yield, 80.6%) of the target compound. The still residue weighed 177.3 g.

Comparative Example 1

Synthesis of Neryldiethylamine Containing 6 wt % α-Neryldiethylamine

The same procedure as in Example 1 was conducted, except that 14.0 ml (140 mmol) of isoprene was used in place of 18.0 ml (180 mmol) of isoprene and that the high-temperature stirring was conducted at 90° C. for 3.5 hours. Thus, the target compound was obtained in an amount of 5.75 g (27.5 mmol; GC yield, 68.7%).

Comparative Example 2

Synthesis of Neryldiethylamine Containing 5 wt % α-Neryldiethylamine

The same procedure as in Example 1 was conducted, except that 12.0 ml (120 mmol) of isoprene was used in place of 18.0 ml (180 mmol) of isoprene and that the high-temperature stirring was conducted at 70° C. for 4 hours. Thus, the target compound was obtained in an amount of 2.87 g (13.7 mmol; GC yield, 34.3%).

Comparative Example 3

Synthesis of Neryldiethylamine Containing 6 wt % α-Neryldiethylamine

The same procedure as in Example 1 was conducted, except that 14.0 ml (140 mmol) of isoprene was used in place of 18.0 ml (180 mmol) of isoprene and that the high-temperature stirring was conducted at 70° C. for 4 hours. Thus, the target compound was obtained in an amount of 4.19 g (20.0mmol; GC yield, 49.9%).

Reaction conditions used in each of the Examples and Comparative Examples and the yields obtained therein are shown in Table 1.

TABLE 1

| Example | Isoprene/ diethyl- amine | Reaction temper- ature (° C.) | Reaction time (hr) | Yield (%) |
| --- | --- | --- | --- | --- |
| Example 1 | 4.5 | 90 | 2.5 | 87.0 (GC) |
| Example 2 | 4.5 | 90 | 3.0 | 85.5 (GC) |
| Example 3 | 4.5 | 80 | 3.0 | 81.8 (GC) |
| Example 4 | 4.5 | 80 | 3.5 | 85.8 (GC) |
| Example 5 | 4.0 | 90 | 3.0 | 77.4 (GC) |
| Example 6 | 4.5 | 90 | 2.5 | 80.6 (isolation) |
| Comparative Example 1 | 3.5 | 90 | 3.5 | 68.7 (GC) |
| Comparative Example 2 | 3.0 | 70 | 4.0 | 34.3 (GC) |
| Comparative Example 3 | 3.5 | 70 | 4.0 | 49.9 (GC) |

Examples 1 to 6 and Comparative Examples 1 to 3 show results of telomerization conducted with the aid of a butyllithium catalyst.

Examples 1 to 6 demonstrated that the telomerization conducted for from 2.5 to 3.5 hours gives neryldiethylamine in a yield as high as from 77.4 to 87.0% when the isoprene/diethylamine ratio is in the range of from 4.0 to 4.5 and the reaction temperature is 80° C. or 90° C. Even when the same butyllithium catalyst was used, a prolonged reaction time of 5.5 hours was necessary at a reaction temperature of 75° C.

Comparative Example 1 shows results of the reaction conducted at a temperature of 90° C. for 3.5 hours using an isoprene/diethylamine ratio reduced to 3.5. The yield was as low as 68.7%. Consequently, the isoprene/diethylamine ratio should be 4.0 or higher.

Comparative Examples 2 and 3 show results of the reaction conducted at a temperature of 70° C. using isoprene/diethylamine ratios reduced to 3.0 and 3.5. The yields were as low as 34.3% and 49.9% when the reaction time was 4 hours. Consequently, in order to cause the reaction to proceed in a short time period, the reaction temperature and the isoprene/diethylamine ratio should be 80° C. or higher and 4.0 or higher, respectively.

Example 7

<Asymmetric Isomerization>

Into a pressure tube in which the atmosphere had been replaced with nitrogen were introduced 297.6 g (1.424 mol) of the neryldiethylamine obtained in Example 6, 377 ml of dry THF, and a THF solution of $[Rh((R)\text{-}t\text{-}BINAP)_2]ClO_4$ (23.2 ml/L; S/C=7000). The THF was recovered at a temperature of 110° C. and ordinary pressure. Thereafter, 337.6 g of a crude enamine was recovered under reduced pressure. The enamine obtained was distilled under reduced pressure (76° C./13.3 Pa) to obtain 294.4 g of (R)-citronellal enamine. Yield, 99.0% (of which α-citronellal enamine accounted for 3.5%).

Example 8

<Asymmetric Isomerization>

The same operation as in Example 7 was conducted except that 5.8 ml of a THF solution of $[Rh((S)\text{-}t\text{-}BINAP)_2]ClO_4$ (0.91 mol/L; S/C=7000) was used in place of $[Rh((R)\text{-}t\text{-}BINAP)_2]ClO_4$. The THF was recovered at a temperature of 110° C. and ordinary pressure. Thereafter, 84.4 g of a crude enamine was recovered under reduced pressure. The enamine obtained was distilled under reduced pressure (76° C./13.3 Pa) to obtain 73.6 g of (S)-citronellal enamine. Yield, 99. 0% (of which α-citronellal enamine accounted for 3.4%).

Example 9
<Hydrolysis>

Into a flask were introduced 294.4 g (1.41 mol) of (R)-citronellal enamine and 300 ml of toluene. Thereto was dropwise added 360 g (0.735 mol) of 20 wt % sulfuric acid solution over 3.5 hours at a reaction temperature of 10° C. or lower. The reaction mixture was stirred for 1.5 hours. After liquid separation, the organic layer was washed with water and 5 wt % aqueous sodium carbonate solution. The solvent was distilled off under reduced pressure and the resultant residue was distilled under reduced pressure (93–94° C./1,870 Pa) to obtain 209.2 g of citronellal. Yield, 90%. Purity, 94.6% (of which α-citronellal accounted for 3.3%).

Example 10
<Hydrolysis>

Into a flask were introduced 73.6 g (1.40 mol) of (S)-citronellal enamine and 75 ml of toluene. Thereto was dropwise added 90 g (0.184 mol) of 20 wt % sulfuric acid solution over 3.5 hours at a reaction temperature of 10° C. or lower. The reaction mixture was stirred for 1.5 hours. After liquid separation, the organic layer was washed with water and 5 wt % aqueous sodium carbonate solution. The solvent was distilled off under reduced pressure and the resultant residue was distilled under vacuum (93–94° C./1,870 Pa) to obtain 52.3 g of citronellal. Yield, 90%. Purity, 94.6% (of which α-citronellal accounted for 3.4%).

Example 11
<Hydrogenation Reaction>

Into a 100-ml autoclave were introduced 20.5 g (132.8 mmol) of (R)-citronellal, 1.0 g (5%, wt/wt) of a copper-chromium catalyst, and 0.04 g (0.2%, wt/wt) of sodium carbonate. After the atmosphere in the system was replaced with hydrogen, the reaction mixture was vigorously agitated in a hydrogen atmosphere (3.4 MPa) at 130° C. for 4.5 hours and then cooled. Thereafter, the catalyst was removed by filtration. The crude citronellol obtained was distilled under reduced pressure (70° C./1,870 Pa) to obtain 15.15 g of (S)-citronellol. Yield, 73%. Purity, 98.6% (of which α-citronellol accounted for 3.4%).

<Sensory Test>

Optically active 3,7-dimethyl-7-octenol, as an impurity, has a rosy fragrance characteristic of aliphatic aldehydes and is excellent in intensity and diffusibility. Optically active 3,7-dimethyl-6-octenol ((S)-citronellol), when containing the 7-octenol compound in an amount of from 2 to 10% by weight, can have a feature of rhodinol, which is an expensive substance isolated from geranium oil and having a mellow fragrance.

According to the invention, a cis-3,7-dimethyl-2,6-octadienylamine compound (nerylamine compound) which contains from 2 to 10% by weight cis-3,7-dimethyl-2,7-octadienylamine compound (α-nerylamine compound) and is useful as a material for perfumes can be obtained in high yield in a short time period. Furthermore, (S)-citronellol, having an excellent fragrance, can be if obtained by asymmetrically isomerizing, hydrolyzing, and hydrogenating the nerylamine compound.

While the invention has been described in detail and with reference to specific embodiments thereof, it will be apparent to one skilled in the art that various changes and modifications can be made therein without departing from the spirit and scope thereof.

This application is based on Japanese patent application No. 2000-106649 filed on Apr. 7, 2000, the entire contents of which incorporated herein by reference.

What is claimed is:

1. A process for producing a cis-3,7-dimethyl-2,6-octadienylamine compound represented by general formula (3):

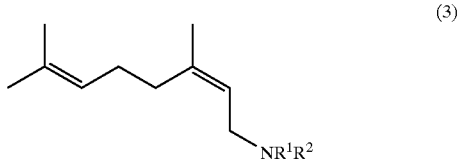

wherein $R^1$ and $R^2$ each represents a hydrogen atom or an alkyl, aralkyl, or aryl group having 1 to 10 carbon atoms, containing from 2 to 10% by weight cis-3,7-dimethyl-2,7-octadienylamine compound represented by general formula (4):

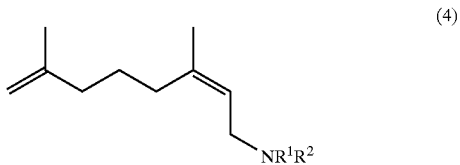

wherein $R^1$ and $R^2$ each represents a hydrogen atom or an alkyl, aralkyl, or aryl group having 1 to 10 carbon atoms, which comprises subjecting a mixture of an alkylamine and isoprene in a molar ratio of from 1:4 to 1:4.5 to telomerization at a reaction temperature of from 80 to 100° C. for from 2.5 to 3.5 hours in the presence of an alkyllithium catalyst and/or phenyllithium catalyst.

2. The process as in claim 1, wherein the alkylamine is selected from the group consisting of dimethylamine, diethylamine, di-n-propylamine, diisopropylamine, di-n-butylamine, cyclohexylamine, piperidine, pyrrolidine, and morpholine.

3. The process as in claim 1, wherein the alkyllithium catalyst is selected from the group consisting of methyllithium, n-butyllithium, sec-butyllithium and tert-butyllithium.

4. The process as in claim 1, wherein the amount of the lithium catalyst to be used in the telomerization is from 0.5 to 5 mol % based on the amine compound to be subjected to the reaction.

5. The process as in claim 1, wherein the telomerization is conducted in an inert atmosphere with a solvent.

* * * * *